United States Patent [19]

Teague et al.

[11] 4,337,172
[45] Jun. 29, 1982

[54] ENHANCED IMMOBILIZATION OF A GLUCOSE ISOMERASE

[75] Inventors: John R. Teague, Darien; Aronson L. Huebner, Woodbridge, both of Ill.

[73] Assignee: UOP Inc., Des Plaines, Ill.

[21] Appl. No.: 225,559

[22] Filed: Jan. 15, 1981

[51] Int. Cl.³ .............................................. B01J 31/06
[52] U.S. Cl. .................................... 252/430; 252/428; 435/176; 435/180
[58] Field of Search ................. 252/428, 430; 435/176, 435/180

[56] References Cited

U.S. PATENT DOCUMENTS 3,909,354  9/1975  Thompson et al. .................. 435/180
4,141,857  2/1979  Levy et al. .......................... 252/430
4,218,363  8/1980  Rohrbach et al. ................... 435/180
4,252,899  2/1981  Enokizono et al. .................. 435/176

Primary Examiner—John F. Niebling
Attorney, Agent, or Firm—James R. Hoatson, Jr.; Eugene I. Snyder; William H. Page, II

[57] ABSTRACT

The immobilization of glucose isomerase onto a support matrix is enhanced by pretreating the support matrix with divalent magnesium ions. In one embodiment, the support matrix is an inorganic oxide impregnated with a polyamine which is subsequently cross-linked with an excess of a bifunctional reagent so as to furnish a plurality of pendant functional groups, and the wash solution is magnesium sulfate.

25 Claims, No Drawings

ENHANCED IMMOBILIZATION OF A GLUCOSE ISOMERASE

BACKGROUND OF THE INVENTION

Enzyme-catalyzed reactions have the advantages of proceeding with great chemical specificity under relatively mild conditions, and often accomplish what man finds difficult, if not impossible, to duplicate in the laboratory. For such reasons there is increasing emphasis on the use of enzymatic processes on a commercial scale. One example, of many which could be cited, is the conversion of glucose to fructose using glucose isomerase.

Enzymes are water soluble, and if they are merely used in aqueous solutions recovery of enzymes for reuse is difficult and expensive. Using the enzyme only once affords a process which is relatively expensive. Consequently, many techniques have been developed for immobilizing the enzyme in such a way that substantial enzymatic activity is displayed while the enzyme itself remains rigidly attached to some water-insoluble support, thereby permitting reuse of the enzyme over substantial periods of time and for substantial amounts of feedstock. One illustration of a method for immobilizing an enzyme is found in U.S. Pat. No. 4,141,857, where a polyamine is absorbed on a metal oxide such as alumina, treated with an excess of a bifunctional reagent, such as glutaraldehyde, so as to cross-link the amine, and then contacting the mass with enzyme to form covalent bonds between the pendant aldehyde groups and an amino group on the enzyme. The support matrix prepared according to the aforementioned invention has great utility in immobilizing reactive chemical entities, enzymes being but one class of such reactive chemical entities.

Generally, immobilized enzyme systems are prepared by contacting a suitable solution containing the enzyme with the support matrix, removing the excess of enzyme solution, and recovering the resulting immobilized enzyme system. Because of the relatively high cost of enzymes, it is highly desirable to maximize enzyme utilization. Among the identifiable characteristics measuring enzyme utilization in an immobilized enzyme system are included the activity and half life of the immobilized enzyme system, and the coupling efficiency of the enzyme to the support matrix. A discovery leading to this invention is that pretreatment of a support matrix with a source of divalent magnesium ions enhances the utilization and immobilization of glucose isomerase.

SUMMARY OF THE INVENTION

The present invention has as an object a method of enhancing the immobilization of glucose isomerase on a support matrix. An embodiment comprises contacting the support matrix with a solution furnishing divalent magnesium ions, removing the excess of said solution, and recovering the resulting magnesium impregnated support matrix. In a more specific embodiment the salt is magnesium sulfate. In a still more specific embodiment the support matrix is impregnated with at least 0.1 millimoles of divalent magnesium ions per gram of support matrix. Other objects and embodiments will be apparent from this subsequent description.

DESCRIPTION OF THE INVENTION

An immobilized enzyme system consists of a support matrix on which there is bound an enzyme. A support matrix is a structure characterized as having good physical integrity and favorable properties toward liquid flow under conditions experienced in fixed bed reactors, and further characterized by having the ability to bind or immobilize enzymes with minimum perturbation of enzymatic action. By an immobilized enzyme system is meant the structure which results from immobilization of an enzyme on a support matrix.

The binding or immobilization of enzymes to support matrices is represented by the extremes of physical and chemical binding forces. It is to be recognized that in most cases enzyme immobilization arises from a combination of such binding forces, although often one such force predominates. The nature of enzyme immobilization generally is determined by the nature of the support matrix. As an example, when the support matrix is a resin, such as one of the phenol formaldehyde type, binding is predominantly through physical forces. A similar result is obtained when the support matrix is of an ion exchange type. Where the support matrix is comprised of refractory inorganic material, such as inorganic oxides, glass, and ceramics, bearing or impregnated with organic material, for example, polyamines, either bearing pendant functional groups themselves or cross-linked with a bifunctional reagent which provides pendant functional groups, enzyme immobilization arises mainly by chemical reaction of a site on the enzyme with the pendant functional group so as to form a covalent bond. In such an instance binding is, at least predominantly, by chemical means.

It is a discovery of this invention that impregnating the support matrix with divalent magnesium ions, such as by contacting the support matrix with a solution furnishing divalent magnesium ions, enhances subsequent immobilization of glucose isomerase onto the support matrix, the enhancement being manifested primarily by an increased half life of the immobilized glucose isomerase. Additionally, pretreatment may result in a decreased time for immobilization of glucose isomerase. It is apparent that manifestation of increased half life is highly advantageous and leads to a substantial improvement in an immobilized glucose isomerase system.

The method of this invention is applicable to all support matrices, regardless of their nature. It is especially applicable to support matrices comprised of porous, refractory inorganic oxides, such as alumina, thoria, magnesia, silica, and combinations thereof, glass, or ceramics bearing or impregnated with a polyamine reacted with an excess of a bifunctional reagent so as to cross-link the polyamine and furnish a plurality of functional groups pendant to the formed polymer. Among the suitable polyamines are included materials such as polyethyleneimine, polypropyleneimine, tetraethylenepentamine, ethylenediamine, diethylenetriamine, triethylenetetramine, pentaethylenehexamine, hexamethylenediamine, phenylenediamine, and amino(-polystyrene), with polyethyleneimine being an especially preferred polyamine. Among the bifunctional reagents used are glutaraldehyde, succindialdehyde, terephthaldehyde, and toluenediisocyanate, glutaraldehyde often being the bifunctional reagent of choice.

Briefly described, the invention herein comprises impregnating a support matrix with divalent magnesium ions, such as by contacting a support matrix with a solution furnishing divalent magnesium ions, removing the excess of said solution, and recovering the resulting magnesium impregnated support matrix. This impregnation of the support matrix with divalent magnesium ions is performed prior to immobilization of glucose isomerase thereon. By "prior to" is meant that such impregnation is a process stage performed before immobilization of the enzyme. It is preferred that the impregnation is performed immediately prior to immobilization, in the context of a process stage and in the context of time. However, it is to be understood that such impregnation may occur earlier, in both contexts, so long as subsequent events do not leach out or otherwise substantially decrease the amount of impregnated magnesium ion.

As stated above, the support matrix is impregnated with divalent magnesium ions by contacting said matrix with a solution containing a source of magnesium ion. Inorganic and organic salts are a convenient source of magnesium ion, and their nature is not critical to the success of this invention so long as they are unreactive toward the support matrix and do not interfere with the activity of the subsequently bound enzyme. Among the salts which may be used are the magnesium halides, such as magnesium chloride, bromide, and iodide, magnesium sulfate, magnesium nitrate, magnesium hypophosphite, magnesium fluorosilicate, magnesium acetate and magnesium lactate. Magnesium sulfate frequently is preferred because of its great solubility and relatively low cost.

The concentration of divalent magnesium ion in the contacting solution is not critical, and at least the upper limit may be dictated by the solubility of the source of the divalent magnesium ions. Concentrations from about 1 to about 25 millimolar in magnesium ion have been found convenient to use, although both higher and lower concentrations are not necessarily deleterious to the practice of this invention.

Of far greater significance is the total amount of divalent magnesium ion impregnated per gram of support matrix. This amount may depend on the type of support matrix used, the temperature of contacting, and the constitution of the enzyme solution offered, among other factors. In general, where the support matrix has not been previously contacted with divalent magnesium ion, or does not independently contain divalent magnesium ion, the support matrix should be impregnated with at least 0.1 millimoles of divalent magnesium ion per gram of support matrix. In a preferred embodiment the support matrix is impregnated with divalent magnesium ion in an amount from about 0.1 to about 2 millimoles ion per gram of support matrix. There does not seem to be an upper limit to the amount of magnesium ion impregnation which is necessary for the practice of this invention, but further increase in impregnation does not necessarily lead to further increments in advantageous effect.

The contact time will depend on such things as the concentration of magnesium in the solution, the support matrix used, and the relative amounts of solution and support matrix. For example, where the support matrix is of the cross-linked polyamine type, and the solution is a 5 millimolar magnesium sulfate solution, and contacting is performed by passing the solution over a bed of the support matrix at a rate such that there is 1 bed volume about every 4 minutes, then equilibrium is attained after about 7 to 8 bed volumes have been passed. Generally, a sufficiently large excess of solution is used so that equilibrium may be attained in from about 15 to about 30 minutes. By equilibrium is meant that state in which the support matrix no longer takes up magnesium from the contacting solution.

The method of this invention is practiced as follows. A solution is prepared from material furnishing a source of divalent magnesium ion. As mentioned previously, inorganic and organic salts of magnesium are the most convenient source of magnesium ions. The support matrix is then contacted with this solution for a sufficient time to insure attainment of equilibrium in impregnation of magnesium ion. The temperature does not seem to have an important effect; contacting may be performed from about 0° C. to about 90° C., and generally is performed at ambient temperature. Such contacting may be as a batch operation, where the support matrix and the solution are mixed at least intermittently. Alternately, the solution may be passed through a fixed bed of the support matrix. Other variations, where contacting is done by fluidized bed, expanded bed, and the like, will be recognized by the skilled artisan.

The practice of this invention is not limited to a particular type of support matrix. In a preferred embodiment, the support matrix is an inorganic oxide impregnated with a polyamine subsequently cross-linked with an excess of a bifunctional reagent so as to furnish a plurality of pendant functional groups. For example, an inorganic oxide, such as gamma alumina, may be contacted with an aqueous solution of a polyamine, such as polyethyleneimine, where the polyamine is present at a concentration from about 1% to about 50%. Excess liquid is removed by suitable means, as by decantation. The oxide may be washed with water to remove excess polyamine, but it is preferred to merely dry the material by evaporation of the water. An aqueous solution of cross-linking agent, such as glutaraldehyde, containing from about 1% to about 25% of the bifunctional reagent is added in an amount sufficient to provide an excess of from about 3 to about 50 or more moles of said bifunctional reagent per mole of polyamine. This solution is contacted, with occasional mixing, with the polyamine-coated oxide for a time sufficient to ensure equilibrium, generally from about 5 minutes to about 5 hours. Liquid is then removed from the oxide support by suitable means, such as by decantation, and the solid support is washed well with water to remove adhering, but not chemically bound, bifunctional reagent.

Where the preferred support matrix is utilized, magnesium impregnation may be performed as described above. However, a variant comprises incorporating a source furnishing divalent magnesium ions into the solution of bifunctional reagent, so that cross-linking, furnishing of a plurality of pendant functional groups, and impregnation with magnesium ion are carried out concurrently.

The immobilized enzyme system such as a glucose isomerase enzyme system may be prepared by contacting the magnesium impregnated support matrix with a solution containing glucose isomerase at a temperature from about 0° C. to about 70° C. for a time sufficient to ensure complete immobilization. Contacting may be performed by intermittent mixing when the operation is done in a batch mode. Alternately, contacting may be done by passing the enzyme solution through a fixed or fluidized bed of the support matrix. Immobilization by other means, such as by an expanded bed, will be apparent to those skilled in the art and such alternate means are intended to be encompassed herein. Immobilization generally is complete within about 30 hours, depending upon the temperature, the immobilization procedure, concentration of enzyme in the offering solution, support matrix, and so forth. After immobilization is complete adhering but unbound enzyme is removed by washing the system with, for example, deionized water, a solution of strong electrolyte, or feedstock.

The following examples are merely illustrative of this invention. It is to be understood that this invention is not to be limited thereto.

EXAMPLES 1 and 2

Support matrices were prepared in the following way. Alumina 400 g of 60/80 mesh, ABD 0.3, was mixed with a 1.5% by weight solution of polyethyleneimine in water in an amount sufficient to yield 0.117 grams polyamine per gram alumina. After thorough mixing, water was evaporated and the polyamine-impregnated alumina was loaded into a glass column of 5 cm I.D.

An aqueous solution of glutaraldehyde, 2.5% by weight, 8 liters total volume, was circulated upflow at 40 ml per minute for 18 minutes, then recycled downflow at 400 ml per minute for 60 minutes. The bed was then washed with deionized water circulating downflow at 400 ml per minute for 4 hours 40 minutes to thoroughly remove excess glutaraldehyde. At the end of this wash the effluent gives a negative fuchsin aldehyde test. The support matrix so prepared is in a state ready for immobilization of enzyme.

When prepared according to the directions above, the matrix is relatively free of magnesium. To prepare a magnesium impregnated matrix, the deionized water wash was replaced by a solution of a magnesium salt. For example, a solution of 0.005 M magnesium sulfate was circulated downflow at 400 ml per minute for 4 hours 40 minutes. After about 30 minutes very little additional magnesium was deposited on the matrix, as shown by the effluent magnesium level being about the same as the initial solution. The resulting support matrix contained 0.13 m moles magnesium per gram of support matrix.

When higher concentrations of magnesium sulfate were used in the wash solution, higher levels of magnesium impregnation are obtained. For example, using a 0.010 M magnesium sulfate solution afforded a matrix containing 1.3 m moles magnesium per gram support matrix.

EXAMPLES 3 and 4

Immobilized glucose isomerase systems were prepared from a magnesium-free support matrix and one impregnated with 0.13 m moles magnesium per gram matrix in the following way. A total of 8.5 liters of an aqueous solution at 60° C. containing 3500 units glucose isomerase per gram support matrix was recycled upflow through a bed of support matrix from 400 g alumina for 25 minutes at 400 ml per minute. Flow was then reversed and the enzyme solution was recycled downflow for 23 hours. Excess adhering but unbound enzyme was removed by washing with a salt solution, prepared by dissolving 12 g magnesium sulfate and 20 g sodium sulfite in 20 liters deionized water, by washing the bed with 6 liters of this solution downflow at 400 ml per minute for 15 minutes. The column was further washed with 4 liters of salt solution recycled upflow for 30 minutes at 400 ml per minute, after which this solution was discarded, and the wash procedure was repeated three more times until the entire salt solution was used.

EXAMPLES 5 and 6

The magnesium-free and magnesium impregnated immobilized glucose isomerase systems prepared as described above were used as fixed bed reactors for the conversion of glucose to fructose. The feedstock was Cerelose feed at 45% by weight dry solids, and conversions were performed at 60° C. under nitrogen and pH 8.0–8.3 to a level of 42% fructose in the effluent. Initial activities for both systems were 2000–2100 units per gram. The half life for the magnesium-free system was 58 days, whereas that for the system impregnated with 0.13 m mole magnesium ion per gram support matrix was 78 days. Thus it is seen that magnesium impregnation at this level increases the half life of the immobilized glucose isomerase system by over 34%.

What is claimed is:

1. A method of enhancing the subsequent immobilization of glucose isomerase onto a support matrix comprising impregnating said matrix, prior to contact with said glucose isomerase, with at least 0.1 millimoles divalent magnesium ion per gram of support matrix, and recovering the resulting magnesium impregnated support matrix.

2. The method of claim 1 wherein impregnating said matrix is effected essentially by contacting said matrix with a solution furnishing divalent magnesium ions, and removing the excess of said solution.

3. The method of claim 2 wherein the solution furnishing divalent magnesium ions is a solution of an inorganic or organic salt of divalent magnesium.

4. The method of claim 3 wherein said salt is selected from the group consisting of magnesium halides, magnesium sulfate, magnesium nitrate, magnesium hypophosphite, magnesium fluorosilicate, magnesium acetate, and magnesium lactate.

5. The method of claim 4 wherein said salt is magnesium sulfate.

6. The method of claim 2 where the solution is from about 1 to 25 millimolar in divalent magnesium ion.

7. The method of claim 1 where the support matrix is impregnated with from about 0.1 to about 2 millimoles of divalent magnesium ion per gram of support matrix.

8. The method of claim 1 wherein the support matrix is an inorganic oxide impregnated with a polyamine cross-linked with an excess of a bifunctional reagent so as to furnish a plurality of pendant functional groups.

9. A method of preparing immobilized glucose isomerase comprising:
   (a) impregnating a porous refractory inorganic oxide with a polyamine;
   (b) contacting the impregnated inorganic oxide with an excess of a bifunctional reagent so as to cross-link the polyamine and furnish a plurality of pendant functional groups;
   (c) removing the excess of said bifunctional reagent;
   (d) impregnating the resulting support matrix with at least 0.1 millimoles divalent magnesium ion per gram support matrix;
   (e) contacting the magnesium impregnated support matrix with a solution containing glucose isomerase at a temperature from about 0° C. to about 70° C. until immobilization is complete; and
   (f) recovering the resulting immobilized glucose isomerase.

10. A method of preparing an immobilized glucose isomerase comprising:
  (a) impregnating a porous refractory inorganic oxide with a polyamine;
  (b) contacting the impregnated inorganic oxide with a solution comprising an excess of a bifunctional reagent and divalent magnesium ions so as to crosslink the polyamine and furnish a plurality of pendant functional groups while impregnating the resulting support matrix with magnesium ions;
  (c) removing the excess of said solution;
  (d) contacting the resulting support matrix with a solution containing glucose isomerase at a temperature from about 0° C. to about 70° C. until immobilization is complete;
  (e) and recovering the resulting immobilized glucose isomerase.

11. The method of claim 9 wherein impregnating said matrix consists essentially of contacting said matrix with a solution furnishing divalent magnesium ions, and removing the excess of said solution.

12. The method of claim 9 or 10 where the inorganic oxide is selected from the group consisting of alumina, thoria, magnesia, silica, and combinations thereof.

13. The method of claim 9 or 10 where the polyamine is selected from the group consisting of polyethyleneimine, polypropyleneimine, tetraethylenepentamine, ethylenediamine, diethylenetriamine, triethylenetetramine, pentaethylenehexamine, hexamethylenediamine, phenylenediamine, and amino(polystyrene).

14. The method of claim 9 or 10 where the bifunctional reagent is selected from the group consisting of glutaraldehyde, succindialdehyde, terephthalaldehyde, and toluenediisocyanate.

15. The method of claim 10 or 11 where the solution furnishing divalent magnesium ions is a solution of an inorganic or organic salt of divalent magnesium.

16. The method of claim 15 wherein said salt is selected from the group consisting of magnesium halides, magnesium sulfate, magnesium nitrate, magnesium hypophosphite, magnesium fluorosilicate, magnesium acetate, and magnesium lactate.

17. The method of claim 16 wherein said salt is magnesium sulfate.

18. The method of claim 10 or 11 wherein the solution containing divalent magnesium ions is from about 1 to about 25 millimolar in divalent magnesium ion.

19. The method of claim 9 or 10 where the support matrix is impregnated with at least 0.13 millimoles divalent magnesium ion per gram of support matrix.

20. An immobilized glucose isomerase system prepared by the method of claim 9 or 10.

21. The immobilized glucose isomerase system of claim 20 where the inorganic oxide is selected from the group consisting of alumina, thoria, magnesia, silica, and combinations thereof.

22. The immobilized glucose isomerase system of claim 20 where the polyamine is selected from the group consisting of polyethyleneimine, polypropyleneimine, tetraethylenepentamine, ethylenediamine, diethylenetriamine, triethylenetetramine, pentaethylenehexamine, hexamethylenediamine, phenylenediamine, and amino(polystyrene).

23. The immobilized glucose isomerase system of claim 22 where the polyamine is polyethyleneimine.

24. The immobilized glucose isomerase system of claim 20 where the bifunctional reagent is selected from the group consisting of glutaraldehyde, succindialdehyde, terephthalaldehyde, and toluenediisocyanate.

25. The immobilized glucose isomerase system of claim 24 where the bifunctional reagent is glutaraldehyde.

* * * * *